United States Patent
O'Sullivan et al.

(10) Patent No.: US 9,468,494 B2
(45) Date of Patent: Oct. 18, 2016

(54) ENHANCED ABLATION AND MAPPING CATHETER AND METHOD FOR TREATING ATRIAL FIBRILLATION

(75) Inventors: Martin O'Sullivan, Long Beach, CA (US); James K. Lee, Pasadena, CA (US); Irma Hill, LaVerne, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 1902 days.

(21) Appl. No.: 11/323,057

(22) Filed: Dec. 30, 2005

(65) Prior Publication Data

US 2006/0111707 A1    May 25, 2006

Related U.S. Application Data

(62) Division of application No. 10/622,221, filed on Jul. 18, 2003.

(51) Int. Cl.
*A61B 18/14* (2006.01)
*B29C 33/52* (2006.01)
(Continued)

(52) U.S. Cl.
CPC ...... *A61B 18/1492* (2013.01); *A61M 25/1029* (2013.01); *B29C 33/52* (2013.01);
(Continued)

(58) Field of Classification Search
CPC .......... A61B 18/1472; A61B 18/1492; A61B 2018/00065; A61B 2018/00243; A61B 2018/00351; A61B 2018/00577; A61B 2018/00839; A61B 2017/00243; A61B 2218/002; A61B 5/0422
USPC .................................. 606/41; 607/119, 122
See application file for complete search history.

(56) References Cited

U.S. PATENT DOCUMENTS

RE34,502 E    1/1994  Webster, Jr.
5,329,923 A   7/1994  Lundquist
(Continued)

FOREIGN PATENT DOCUMENTS

EP    1498080 A1    1/2005
WO    WO 95/02995   2/1995
(Continued)

OTHER PUBLICATIONS

European Search Report dated Dec. 2, 2004 for European Application No. 04254306.6.
(Continued)

*Primary Examiner* — Michael Peffley
*Assistant Examiner* — Samantha Good
(74) *Attorney, Agent, or Firm* — Lewis Roca Rothgerber Christie LLP

(57) ABSTRACT

A catheter for ablating tissue is provided. The catheter comprises an elongated generally-tubular catheter body having proximal and distal ends. An electrode assembly is provided at the distal end of the catheter body. The electrode assembly including a porous electrode arrangement that is generally transverse to the catheter body. The porous electrode arrangement comprises one or more electrodes electrically connected to a suitable energy source and a porous sleeve mounted in surrounding relation to the one or more electrodes and defining an open space between the porous sleeve and the one more electrodes. One or more irrigation openings fluidly connect the open space to a lumen extending through the catheter through which fluid can pass. In use, fluid passes through the lumen in the catheter, through the one or more irrigation openings, into the open space and through the porous sleeve.

4 Claims, 4 Drawing Sheets

(51) Int. Cl.

| | |
|---|---|
| *B29C 41/10* | (2006.01) |
| *C08G 73/10* | (2006.01) |
| *A61B 5/042* | (2006.01) |
| *A61B 18/00* | (2006.01) |
| *A61B 17/00* | (2006.01) |
| *A61M 25/10* | (2013.01) |
| *B29C 33/38* | (2006.01) |
| *B29C 35/08* | (2006.01) |
| *B29C 41/14* | (2006.01) |
| *B29C 67/00* | (2006.01) |
| *B29L 31/00* | (2006.01) |

(52) U.S. Cl.
CPC .............. *B29C 41/10* (2013.01); *C08G 73/10* (2013.01); *A61B 5/0422* (2013.01); *A61B 2017/00243* (2013.01); *A61B 2018/00065* (2013.01); *A61B 2018/00351* (2013.01); *A61B 2018/00839* (2013.01); *A61B 2018/1472* (2013.01); *A61B 2218/002* (2013.01); *A61M 25/1027* (2013.01); *A61M 25/1038* (2013.01); *B29C 33/3842* (2013.01); *B29C 35/08* (2013.01); *B29C 41/14* (2013.01); *B29C 67/0051* (2013.01); *B29C 2033/525* (2013.01); *B29C 2035/0827* (2013.01); *B29L 2031/7542* (2013.01)

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,480,422 A | 1/1996 | Ben-Haim |
| 5,546,951 A | 8/1996 | Ben-Haim |
| 5,558,091 A | 9/1996 | Acker et al. |
| 5,568,809 A | 10/1996 | Ben-Haim |
| 5,755,760 A | 5/1998 | Maguire et al. |
| 5,779,669 A | 7/1998 | Haissaguerre et al. |
| 5,800,428 A | 9/1998 | Nelson et al. |
| 5,885,278 A | 3/1999 | Fleischman |
| 5,897,529 A | 4/1999 | Ponzi |
| 5,961,513 A | 10/1999 | Swanson et al. |
| 5,964,757 A | 10/1999 | Ponzi |
| 6,068,653 A * | 5/2000 | LaFontaine .................. 607/116 |
| 6,090,104 A * | 7/2000 | Webster, Jr. .................. 606/41 |
| 6,120,476 A | 9/2000 | Fung et al. |
| 6,123,699 A | 9/2000 | Webster, Jr. |
| 6,161,543 A | 12/2000 | Cox et al. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,203,525 B1 | 3/2001 | Whayne et al. |
| 6,210,407 B1 | 4/2001 | Webster |
| 6,267,746 B1 | 7/2001 | Bumbalough |
| 6,371,955 B1 | 4/2002 | Fuimaono et al. |
| 6,405,078 B1 * | 6/2002 | Moaddeb et al. ............. 604/21 |
| 6,475,214 B1 * | 11/2002 | Moaddeb ........................ 606/41 |
| 6,628,976 B1 | 9/2003 | Fuimaono et al. |
| 6,671,561 B1 * | 12/2003 | Moaddeb ........................ 607/120 |
| 6,731,955 B2 | 5/2004 | Hirano et al. |
| 6,986,769 B2 * | 1/2006 | Nelson et al. .................. 606/41 |
| 7,588,568 B2 | 9/2009 | Fuimaono et al. |
| 2003/0060822 A1 | 3/2003 | Schaer et al. |
| 2005/0015082 A1 * | 1/2005 | O'Sullivan et al. ............ 606/41 |

FOREIGN PATENT DOCUMENTS

| | | |
|---|---|---|
| WO | WO 96/05758 | 2/1996 |
| WO | WO 97/24983 | 7/1997 |
| WO | WO 98/29033 | 7/1998 |

OTHER PUBLICATIONS

Haissaguerre, et al. "Spontaneous Initiation of Atrial Fibrillation by Ectopic Beats Originating in the Pulmonary Veins," *The New England Journal of Medicine*, vol. 339 No. 10, pp. 659-666, Sep. 3, 1998.

\* cited by examiner

ENHANCED ABLATION AND MAPPING CATHETER AND METHOD FOR TREATING ATRIAL FIBRILLATION

CROSS-REFERENCE TO RELATED APPLICATION(S)

This application is a divisional of U.S. patent application Ser. No. 10/622,221, entitled ENHANCED ABLATION AND MAPPING CATHETER AND METHOD FOR TREATING ATRIAL FIBRILLATION, filed Jul. 18, 2003, the entire contents of which is incorporated herein by reference.

FIELD OF THE INVENTION

The present invention relates to an improved steerable electrode catheter having an irrigated ablation electrode that is particularly useful for treating atrial fibrillation.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. It is believed that to treat atrial fibrillation by radio-frequency ablation using a catheter, continuous linear lesions must be formed to segment the heart tissue. By segmenting the heart tissue, no electrical activity can be transmitted from one segment to another. Preferably, the segments are made too small to be able to sustain the fibrillatory process. A preferred technique for treating atrial fibrillation by radio-frequency ablation would be a "branding iron" approach, where a relatively long electrode can be held stationary in good contact with the heart wall while ablation is completed. In this way, a continuous transmural burn may be effected.

U.S. Pat. No. 5,800,428 to Nelson et al. discloses a radio frequency ablation catheter system having a flexible, tubular electrode for creating a continuous linear lesion. The tubular electrode is selectively extendable from the distal end of the catheter. The catheter further comprises mechanisms for remotely manipulating and extending the electrode. However, having an extendable electrode house in the catheter provides less degrees of freedom with respect to the shape, size and length of the tubular electrode. Moreover, the physician has to deal with additional moving and manipulatable parts, adding complexity to the procedure. Further, a retractable electrode can cause contamination because blood or coagulate on the electrode can be pulled into and entrapped inside the catheter. The entrapped coagulate can also affect the ability of the electrode to be further extended and retracted. Accordingly, it would be desirable to provide a catheter design having an electrode for creating linear lesions that overcomes these drawbacks.

U.S. patent application Ser. No. 10/199,525, entitled "Atrial Ablation Catheter and Method for Treating Atrial Fibrillation" discloses a catheter having an ablation assembly bent relative to the catheter body and comprising a generally-straight non-retractable tubular electrode formed of a material having shape-memory having at least one irrigation port through which fluid can pass from the inside to the outside of the electrode. However, in order to create lesions that are sufficiently deep to treat arrhythmias, a relatively high level of radio frequency power is often needed, which can result in coagulum formation and tissue charring. The irrigation ports in the tubular electrode described in U.S. patent application Ser. No. 10/199,525 permit the use of cooling fluid to reduce coagulum formation and tissue charring. However, if the irrigation is not efficiently delivered to the tissue being treated, local hot spots can develop at the tissue/electrode interface. Accordingly, a need exists for an improved catheter containing an elongated electrode that can provide more efficient cooling during ablation.

SUMMARY OF THE INVENTION

The invention is directed to an improved catheter and method for ablating linear lesions while ensuring delivery of cooling saline to the tissue being ablated. In one embodiment, the invention is directed to a catheter comprising an elongated generally-tubular catheter body having proximal and distal ends. An electrode assembly is provided at the distal end of the catheter body. The electrode assembly includes a porous electrode arrangement that is generally transverse to the catheter body. The porous electrode arrangement comprises one or more electrodes electrically connected to a suitable energy source and a porous sleeve mounted in surrounding relation to the one or more electrodes and defining an open space between the porous sleeve and the one more electrodes. One or more irrigation openings fluidly connect the open space to a lumen extending through the catheter through which fluid can pass. In use, fluid passes through the lumen in the catheter, through the one or more irrigation openings, into the open space and through the porous sleeve.

In another embodiment, the invention is directed to a catheter comprising an elongated generally-tubular catheter body having proximal and distal ends. An electrode assembly is provided at the distal end of the catheter body. The electrode assembly comprises a non-conductive tubing mounted on the distal end of the catheter body and having a lumen extending therethrough. A generally-straight porous electrode is mounted on the non-conductive tubing and is generally transverse to the axis of the catheter body. The porous electrode comprises one or more electrodes electrically connected to a suitable energy source and a porous sleeve mounted in surrounding relation to the one or more electrodes and defining an open space between the porous sleeve and the one more electrodes. One or more irrigation openings fluidly connect the open space to the lumen extending through the non-conductive tubing.

The invention is also directed to a method for ablating heart tissue. The method comprises inserting the distal end of a catheter as described above into the heart of a patient and forming at least one linear lesion in the atrial tissue with the porous electrode by simultaneously supplying ablation energy to the one or more electrodes and introducing fluid through the irrigation openings so that the fluid passes through the porous sleeve.

In another embodiment, the invention is directed to a method for treating atrial fibrillation. The method comprises inserting the distal end of a catheter as described above into an atrium of the heart of a patient and forming at least one linear lesion in the atrial tissue with the porous electrode by simultaneously supplying ablation energy to the one or more electrodes and introducing fluid through the irrigation openings so that the fluid passes through the porous sleeve.

DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
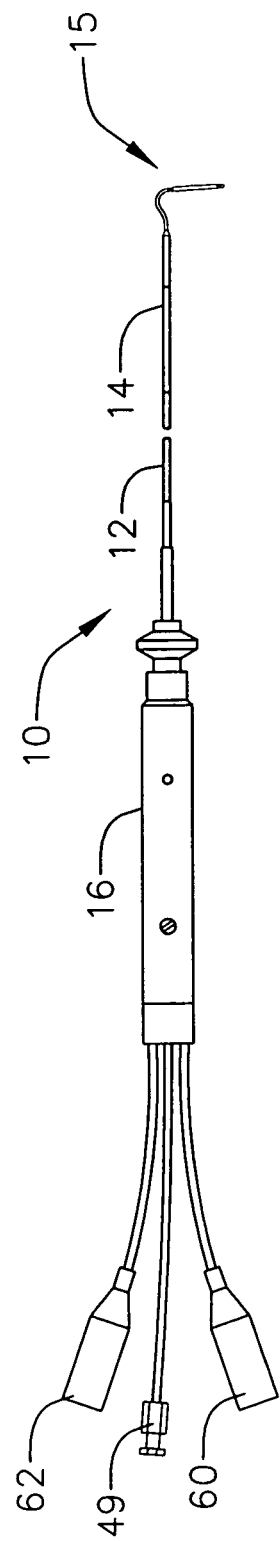
FIG. 1 is a side cross-sectional view of an embodiment of the catheter of the invention.

The invention provides a catheter having an irrigated tubular ablation electrode. As shown in FIG. 1, the catheter comprises an elongated catheter body 10 having proximal and distal ends with an electrode assembly 15 mounted at the distal end of the catheter body and a control handle 16 at the proximal end of the catheter body.

Figure 2:
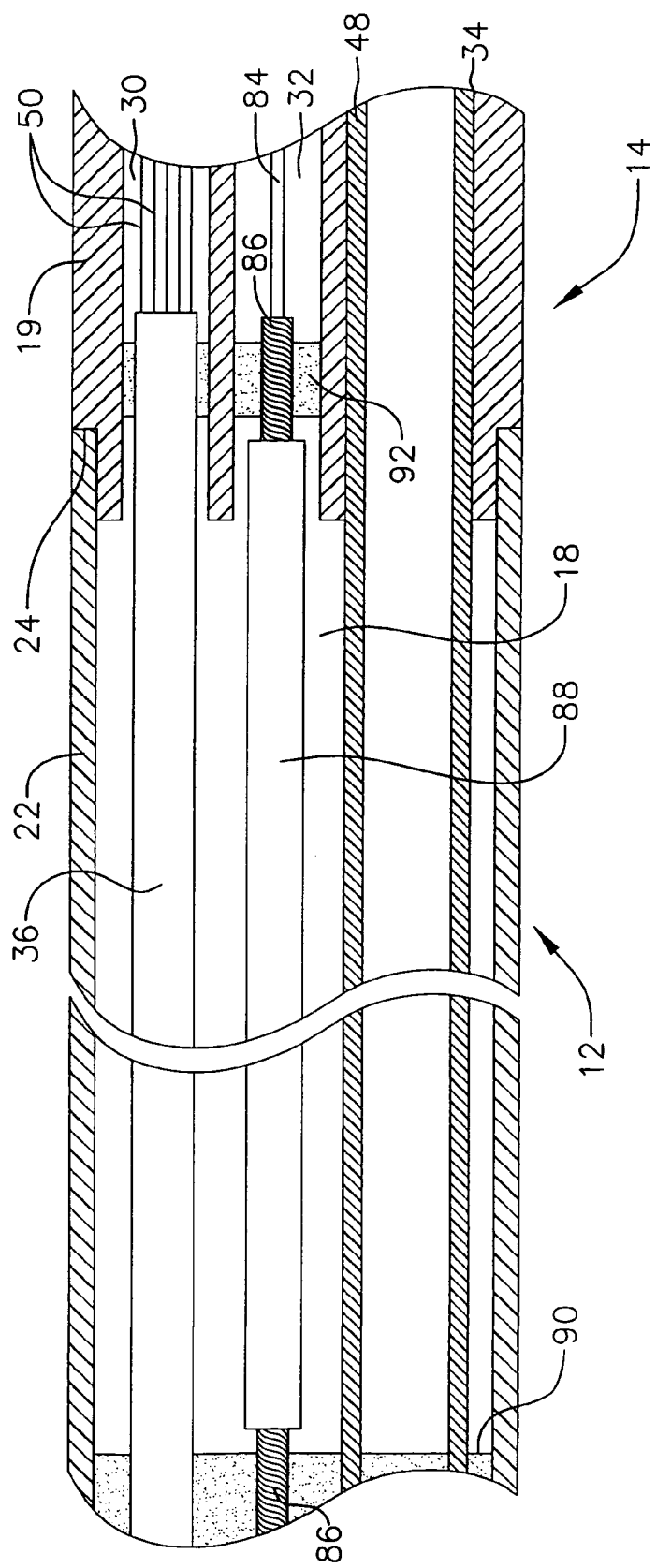
FIG. 2 is a side cross-sectional view of a catheter body according to the invention, including the junction between the proximal shaft and distal shaft.

With reference to FIG. 2, the catheter body 10 comprises an elongated tubular construction having a relatively long proximal shaft 12 and a relatively short distal shaft 14. The proximal shaft 12 has a single, axial or central lumen 18. The proximal shaft 12 is flexible, i.e., bendable, but substantially non-compressible along its length. The proximal shaft 12 can be of any suitable construction and made of any suitable material. A presently preferred construction comprises an outer wall 22 made of polyurethane or PEBAX®. The outer wall 22 comprises an imbedded braided mesh of stainless steel or the like to increase torsional stiffness of the proximal shaft 12 so that, when the control handle 16 is rotated, the distal shaft 14 will rotate in a corresponding manner.

The outer diameter of the proximal shaft 12 is not critical, but is preferably no more than about 8 french, more preferably 7 french. Likewise the thickness of the outer wall 22 is not critical, but is thin enough so that the central lumen 18 can accommodate an infusion tube, a puller wire, lead wires, and any other wires, cables or tubes. If desired, the inner surface of the outer wall 22 is lined with a stiffening tube (not shown) to provide improved torsional stability. In the depicted embodiment, the distal shaft 14 comprises a short section of tubing 19 having three lumens, namely, a lead wire lumen 30, a puller wire lumen 32, and an infusion lumen 34. The wires and tube are described in more detail below. The tubing 19 is made of a suitable non-toxic material that is preferably more flexible than the proximal shaft 12. A presently preferred material for the tubing 19 is braided polyurethane, i.e., polyurethane with an embedded mesh of braided stainless steel or the like, that is more flexible than the catheter body. The number and size of the lumens is not critical and can vary depending on the various wires, tubes and other components carried by the catheter. In a preferred embodiment, the distal shaft 14 has an outer diameter ranging from about 5 french (0.066 inch) to 8 french (0.105 inch), and the lead wire lumen 30 and puller wire lumen 32 are generally about the same size, each having a diameter of from about 0.020 inch to about 0.024 inch, preferably 0.022 inch, with the infusion lumen 34 having a slightly larger diameter of from about 0.032 inch to about 0.038 inch, preferably 0.035 inch.

One means for attaching the proximal shaft 12 to the distal shaft 14 is illustrated in FIG. 2. The proximal end of the distal shaft 14 comprises an outer circumferential notch 24 that receives the inner surface of the outer wall 22 of the proximal shaft 12. The distal shaft 14 and proximal shaft 12 are attached by glue or the like. Other arrangements for joining the proximal and distal shafts are considered within the scope of the invention. For example, the proximal and distal shafts can be made from a single tubing so that the proximal and distal shafts include the same number of lumens. Alternatively, if a stiffening tube is provided, the stiffening tube can extend slightly beyond the distal end of the proximal shaft 12 (e.g., about 3 mm) and be glued to the proximal shaft, with the proximal end of the distal shaft 14 cored out to receive the distal end of the stiffening tube, creating a lap joint. The lap joint and the butt joint formed between the distal end of the proximal shaft 12 and the proximal end of the distal shaft 14 can be secured with polyurethane glue or the like. In another alternative, the proximal shaft 12 can be thermally fused to the distal shaft 14.

If desired, a spacer (not shown) can be located within the proximal shaft 12 at its distal end, adjacent the proximal end of the distal shaft 14. The spacer provides a transition in flexibility at the junction of the proximal shaft and distal shaft, which allows this junction to bend smoothly without folding or kinking. A catheter having such a spacer is described in U.S. Pat. No. 5,964,757, the disclosure of which is incorporated herein by reference.

Figures 3, 4:
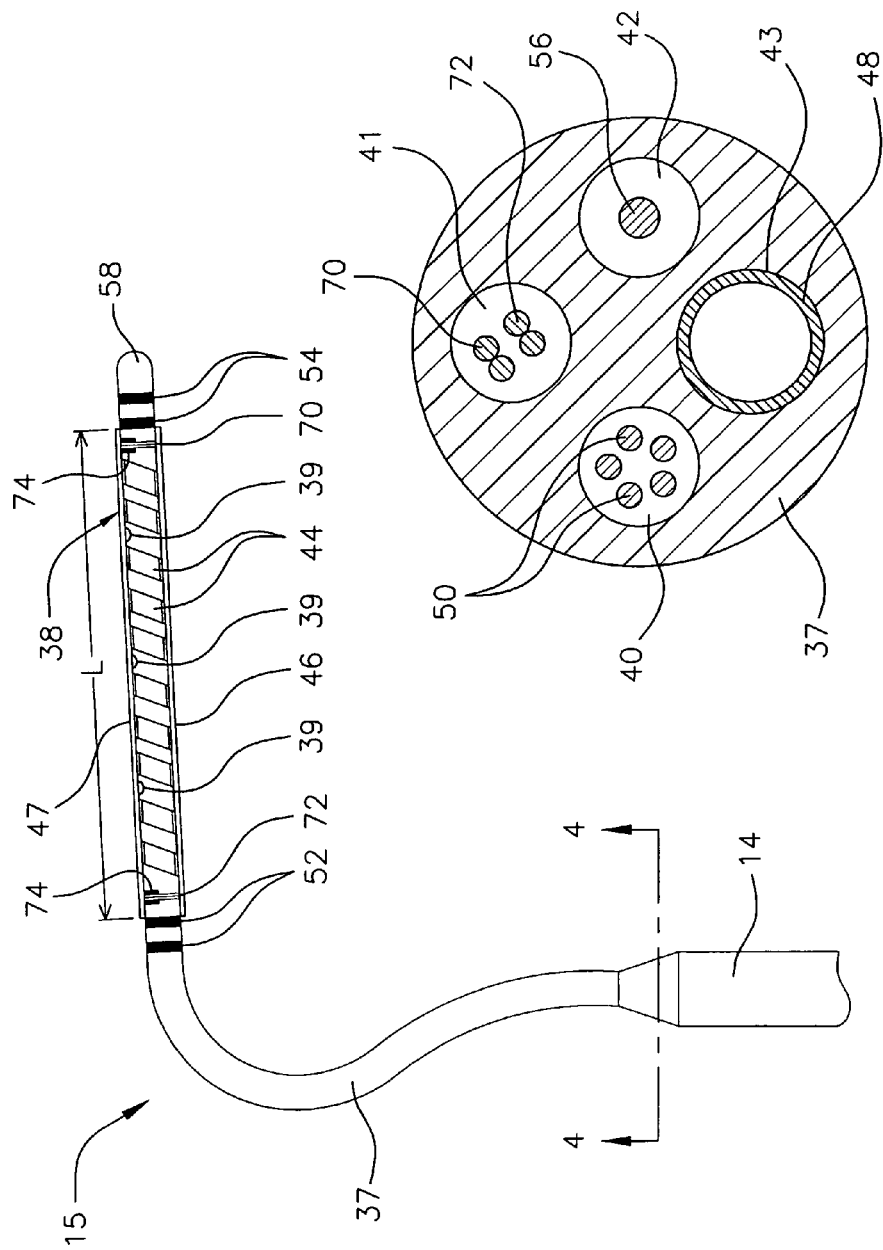
FIG. 3 is a side view of an electrode assembly according to the invention.
FIG. 4 is an end cross-sectional view of the electrode assembly of FIG. 3 along line 4-4.

At the distal end of the distal shaft 14 is a non-retractable electrode assembly 15, as shown in FIGS. 3 and 4. The electrode assembly 15 has proximal and distal ends and comprises an elongated non-conductive tubing 37 mounted on the distal end of the distal shaft 14 and an elongated, porous electrode 38 at the distal end of the non-conductive tubing. In the depicted embodiment, the porous electrode 38 is generally straight and generally transverse to the catheter body 10, and preferably forms an angle with the axis of the catheter body ranging from about 75° to about 110°.

The proximal end of the non-conductive tubing 37 is generally coaxial with the catheter body 10, and the midsection of the non-conductive tubing forms a curve that first bends away from and then back toward and past the axis of the catheter body, with the porous electrode 38 mounted over the straight distal end of the non-conductive tubing, as best shown in FIG. 3. This "foot" or "heel" shape is particularly suitable for ablating a linear lesion with the porous electrode 38 due to its inherent stability. Specifically, it limits the electrode roll when longitudinal push forces are applied to the catheter body, particularly when the porous electrode is placed against the uneven contours of the heart wall. Thus, when the user exerts a longitudinal force on the catheter body, the entire length of the porous electrode tends to exert a force on the tissue rather than the proximal end of the porous electrode being pushed into the tissue and the distal end of the porous electrode being forced away from the tissue.

The generally straight shape of the porous electrode 38 is particularly suitable for creating long linear lesions. However, other shapes for the electrode assembly 15 are also contemplated within the scope of the invention, such as where the porous electrode 38 is curved or bent. A curved porous electrode 38 could be used for creating curved lesions for pulmonary vein isolation. Other electrode assembly shapes that can be used for the invention are described in U.S. Pat. No. 6,371,955, the disclosure of which is incorporated herein by reference.

The non-conductive tubing 37 is generally tubular and includes four lumens, namely, a lead wire lumen 40, a thermocouple lumen 41, a stiffening wire lumen 42 and an irrigation lumen 43. As will become apparent, the number and sizes of the lumens in the non-conductive tubing are not critical and can vary depending on the desired application. The non-conductive tubing 37 can be made of any suitable biocompatible plastic, such as polyurethane or PEBAX®.

The porous electrode 38 comprises one or more electrodes mounted over the non-conductive tubing 37 and covered by a porous material. In the depicted embodiment, a single coiled ribbon electrode 44 is mounted in surrounding relating to the non-conductive tubing 37. The ribbon electrode 44 can be made of any suitable electrically-conductive metal or other material, such as platinum or gold, and can be an alloy, such as a platinum-iridium alloy. Alternatively, the ribbon electrode 44 can be replaced with a series of ring electrodes or with a thin metal coating that is deposited directly onto the non-conductive tubing 37. Other electrode arrangements are contemplated within the scope of the invention.

The non-conductive tubing includes a series of irrigation openings 39 in the region of the ribbon electrode 44. In the depicted embodiment, three irrigation openings 39 are provided between the turns of the ribbon electrode 44. The irrigation openings 39 fluidly connect the irrigation lumen 43 of the non-conductive tubing 37 to the outside non-conductive tubing. Preferably the irrigation openings 39 are located only on the side of the porous electrode 38 that is to be in contact with the tissue to be ablated, which is typically the side facing away from the catheter body 10. The irrigation openings 39 can be any suitable shape, such as rectangular or ovular slots or round holes. In an exemplary embodiment, a space of approximately 3.5 mm is provided between the centers of the irrigation openings 39. As would be recognized by one skilled in the art, the precise number, size, shape and arrangement of irrigation ports 39 can vary as desired.

A porous sleeve 46 is mounted in surrounding relation to the ribbon electrode 44. The porous sleeve 46 is made of a material through which fluid can pass. The proximal and distal ends of the porous sleeve 46 extend beyond the proximal and distal ends of the ribbon electrode 44. As discussed further below, the proximal and distal ends of the porous sleeve 46 are sealed over the non-conductive tubing 37 to create an open space 47 between the porous sleeve and the non-conductive tubing and ribbon electrode 44.

With this design, saline or other fluid can pass out through the irrigation openings 39 between the coils of the ribbon electrode 44 into the open space 47 defined by the porous sleeve 46 and then through the porous sleeve. When radio frequency (RF) energy or other appropriate energy is supplied to the ribbon electrode 44, the RF current is carried to cardiac tissue by saline flow through the porous sleeve 46 while the porous sleeve is in contact with the tissue. The RF current resistively heats the tissue in contact with the porous sleeve 46, causing permanent cellular necrosis of the tissue, thereby creating a linear lesion. The porous sleeve 46 allows for the flow of saline around the ribbon electrode 44 to keep the electrode temperature low during energy application.

This design permits safe delivery of higher levels of RF power that are required to create lesions deep enough to treat arrhythmias such as atrial fibrillation, atrial flutter and ventricular tachycardia. Although with other irrigated electrode designs it is possible for coagulum formation and tissue charring to occur due to inefficient irrigation that results in local hot spots at the tissue/electrode interface, the porous sleeve electrode design ensures that RF current cannot be delivered to the tissue without the presence of the cooling saline or other fluid. Therefore RF lesions can be created only at locations that are also cooled by the saline irrigation.

As noted above, the porous sleeve 46 is made of a material through which saline and other fluid can pass. Preferably the porous sleeve 46 is formed of a generally non-compressible material. As used herein, the term "non-compressible" means that the material generally does not exhibit appreciable or sufficient compressibility between its inner and outer surfaces to conform to surface irregularities of the tissue against which the porous electrode is placed. A particularly suitable material for the porous sleeve 46 is expanded polytetrafluoroethylene (ePTFE), although the sleeve can also be made of other porous materials, such as porous polyethylene, porous silicon, porous urethane, porous nylon, sintered ceramics, and tight weaves of dacron and other woven meshes. Such porous materials are formed using conventional techniques, such as, for example by blowing the material or by drilling micro holes within the material. The porosity of the material desirably ranges between about 5 and 50 microns.

In a particularly preferred embodiment, the porous sleeve 46 comprises ePTFE having an inner diameter of 0.080 inch and an outer diameter of about 0.096 inch, with the ePTFE being expandable to no more than 10% at a distilled water flow rate of 30 to 40 cc/min. The porous electrode preferably has a length L ranging from about 10 to about 25 mm, more preferably from about 10 to about 15 mm, still more preferably about 11 mm. In one embodiment, the degree of porosity of the porous sleeve 46 over its length is generally uniform. This uniformity coupled with the flow restrictiveness of the material results in the fluid emanating from the porous sleeve 46 in a generally even flow over its entire outer surface.

An infusion tube 48 is provided for infusing fluid, such as saline, to the irrigation openings 39. The infusion tube 48 is preferably made of a biocompatible plastic, such as polyimide. The infusion tube 48 has a distal end anchored in the proximal end of the irrigation lumen 43 of the non-conductive tubing 37. The infusion tube 48 extends through the infusion lumen 34 of the distal shaft 14, through the proximal shaft 12, out the proximal end of the control handle 16, and terminates in a luer hub 49 or the like at a location proximal to the control handle. In an alternative arrangement, a single lumen side arm (not shown) is fluidly connected to the central lumen 18 near the proximal end of the catheter body 10, as described in more detail in U.S. Pat. No. 6,120,476, the entire disclosure of which is incorporated herein by reference. Alternatively, the infusion tube 48 can terminate within the distal end of the infusion lumen 34 of the distal shaft 14, with a second infusion tube (not shown) provided that extends from the proximal end of the infusion lumen, through the proximal shaft 12 and out through the control handle 16. Such a design is also described in more detail in U.S. Pat. No. 6,120,476.

An electrode lead wire 50 is attached to the ribbon electrode 44 for electrical connection to a suitable connector (not shown), which is attached to a source of ablation energy, such as RF energy (not shown). The electrode lead wire 50 is soldered, welded or otherwise attached to the ribbon electrode 44. The electrode lead wire 50 can comprise any suitable material, and is preferably a copper wire or a Monel wire with an appropriate non-conductive covering over most of its length. The electrode lead wire 50 for the ribbon electrode 44 extends through the lead wire lumen 40 of the non-conductive tubing 37, the lead wire lumen 30 of the distal shaft 14, the central lumen 18 of the proximal shaft 12, the control handle 16, and is connected to a suitable source of ablation energy (not shown) by means of an appropriate connector as is generally known in the art.

One or more mapping electrodes are mounted over the non-conductive tubing 37. The mapping electrodes enable the user to perform pace mapping to assess tissue contact as well as electrical conductivity within the atrium or other region being treated before and after ablation. In the depicted embodiment two proximal mapping electrodes 52 are mounted proximal to the porous electrode 38, and two distal mapping electrodes 54 are mounted distal to the tubular electrode. Each of the proximal and distal mapping electrodes 52 and 54 comprises a ring electrode that is mounted in surrounding relation to the non-conductive tubing 37, although other electrode arrangements are considered within the scope of the invention. The ring electrodes can be made of any suitable material, and are preferably made of platinum or an alloy of platinum and iridium. An electrode lead wire 50 is welded, soldered or otherwise attached to each of the mapping electrodes 52 and 54. Each mapping electrode 52 and 54 preferably has a length ranging from about 0.5 mm to about 2 mm, more preferably from about 0.5 mm to about 1 mm. The spaces between the mapping electrodes 52 and 54, as well as the spaces between the mapping electrodes and the porous electrode 38, preferably range from about 0.5 mm to about 3 mm, more preferably from about 0.5 mm to about 1.5 mm.

To maintain the desired shape of the non-conductive tubing 37 and porous electrode 38, a stiffening wire 56 is provided within the stiffening wire lumen 42 of the non-conductive tubing. The stiffening wire 56 is made of a material having shape-memory, i.e., that can be straightened or bent out of its original shape upon exertion of a force and is capable of substantially returning to its original shape upon removal of the force. A particularly preferred material for the stiffening wire is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. The stiffening wire 56 can have any desired cross-sectional area and need not be circular. The stiffening wire 56 can be pre-shaped to the desired shape using a heat-treating process, as is generally known in the art. Alternatively, the stiffening wire 56 can be eliminated, and the non-conductive tubing can be pre-shaped in the desired configuration.

Additionally, one or more temperature sensing means can be provided for measuring the electrode/tissue interface temperatures near the porous electrode 38 during ablation. Any conventional temperature sensing means, e.g., a thermocouple or thermistor, may be used. In the depicted embodiment, two thermocouples 70 and 72 are provided. Specifically, a distal thermocouple 70 is provided distal to the porous electrode 38, and a proximal thermocouple 72 is provided proximal to the porous electrode, as described in more detail below. As would be recognized by one skilled in the art, other temperature sensing designs can be used, or the temperature sensors can be eliminated altogether.

To make the electrode assembly 15 described above, an appropriate length of an ePTFE sleeve (for example, around 15 mm) is cut, and five holes are drilled about 1 mm from each end of the ePTFE sleeve evenly about its circumference. A stainless steel mandrel having a Teflon tubing mounted over it is introduced through the ePTFE sleeve. Polyurethane glue is applied to one end of the ePTFE sleeve to form a 1 mm band, and a small rubber O-ring is slid over the band of polyurethane glue to compress the end of the ePTFE sleeve onto the Teflon over the mandrel. Once the polyurethane glue has cured, the O-ring, Teflon and mandrel are removed. V-shaped notches are cut into each end of the ePTFE sleeve.

The ribbon electrode 44 is formed by wrapping a platinum ribbon around a 0.065 inch gauge pin about 10 times, with no gaps between the turns of the coil. The coil is removed from the pin, and the remaining, uncoiled platinum ribbon is cut off from the coil. Platinum rings are welded to the ends of the wound coil.

The non-conductive tubing 37 is cut to an appropriate length, for example, about 40 mm. The three irrigation openings 39 are drilled into the irrigation lumen 43 of the non-conductive tubing 37 at locations 11 mm, 14.5 mm and 18 mm from what is to be the distal end of the non-conductive tubing. The proximal end of the irrigation lumen 43 is trepanned to expand the lumen so that the infusion tube 48 will fit about 2 mm into the irrigation lumen.

Three electrode lead wires 50, two for the proximal ring electrodes 52 and one for the ribbon electrode 44, are introduced into the lead wire lumen 40 of the non-conductive tubing 37. Five lead wire access holes are punched into the non-conductive tubing 37 using a needle, with two positioned about 7 to 8 mm from the distal end of the non-conductive tubing and three positioned about 20 to 22 mm from the distal end of the non-conductive tubing. The three lead wires 50 are pulled out of the three more proximal holes, and the insulation is removed from the tips of the lead wires. Two of the electrode lead wires 50 are welded to two platinum rings to form the proximal ring electrodes 52. The third electrode lead wire 50 is welded to what is to be the proximal end of the platinum coil that forms the ribbon electrode 44. The two platinum rings are than loaded over the non-conductive tubing 37 and aligned with the two most proximal punched holes. The platinum coil is loaded over the non-conductive tubing 37 and aligned with the third most proximal punched hole. The coil is adjusted so that the turns are evenly spaced with the three irrigation openings 39 positioned between the turns, and the platinum coil is anchored in place by applying polyurethane glue to the proximal and distal ends of the ribbon electrode 44.

Two thermocouple wire holes are punched into the thermocouple lumen 41 of the non-conductive tubing 37 approximately 10 mm and 19 mm from the distal end of the non-conductive tubing, i.e., as positions just proximal and distal to the ribbon electrode 44. Two thermocouple wire pairs, such as a constantan wire and a copper wire, are introduced into the thermocouple lumen 41 and pulled through the thermocouple wire holes. The insulation is scraped from the distal ends of the thermocouple wires and the two wires of each pair are soldered together at their distal ends. A short piece of insulating polyimide tubing 74 is inserted over the distal end of each thermocouple wire pair, held in place with polyurethane glue, and cut to a length of about 0.75 mm. The distal ends of the thermocouples 70 and 72 are wrapped around the outside of the non-conductive tubing 37 and glued in place.

The ePTFE sleeve, prepared as described above, is loaded over the platinum coil, which is mounted over the non-conductive tubing 37. The V-shaped notches in the ePTFE sleeve are aligned with the punched holes for the electrode lead wires 50. Two additional electrode lead wires 50 are introduced into the lead wire lumen 40 of the non-conductive tubing 37, pulled out through the two most distal punched holes, and welded to the undersides of two platinum rings to form the two distal mapping electrodes 54. A 1 mm wide band of polyurethane glue is applied to the non-conductive tubing 37 about 22 mm from its distal end. The ePTFE sleeve is slid under the two proximal mapping electrodes 52 and over the band of glue, with the lead wires being aligned in the V-shaped notch in the proximal end of the ePTFE sleeve. Additional polyurethane glue is applied around the proximal end of the ePTFE sleeve. Another 1 mm wide band of polyurethane glue is applied over the non-conductive tubing about 7 mm from its distal end. Nylon thread is wrapped around the distal end of the ePTFE sleeve to adhere the ePTFE sleeve to the second glue band. The nylon thread is removed, and the two distal mapping electrodes 54 are slid over the distal end of the ePTFE sleeve. Additional polyurethane glue is applied over the distal end of the ePTFE sleeve.

A 0.019 inch pre-shaped Nitinol stiffening wire 56 is introduced into the stiffening wire lumen 42 of the non-conductive tubing 37, and the Nitinol wire is cut flush with the proximal end of the non-conductive tubing. The infusion tube 48 is loaded into the trepanned (proximal) end of the irrigation lumen 43 of the non-conductive tubing 37. Polyurethane glue is applied to the proximal end of the non-conductive tubing 37 to seal all lumens except for the irrigation lumen 43, thereby bonding the infusion tube 47 in place. If desired, a plastic blocker can be inserted into the irrigation lumen 43 during manufacturing to prevent glue from entering into the irrigation lumen.

The distal end of the non-conductive tubing 37 is cut a distance of about 0.5 mm to about 1 mm from the most distal mapping electrode 54. Polyurethane glue is applied to the distal end of the non-conductive tubing 37, with some of the glue being allowed to migrate a short distance into the distal end of the lumens in the non-conductive tubing. After curing for about an hour, additional polyurethane glue is added to build up a ball tip 58 at the distal end of the non-conductive tubing 37, thereby forming an atraumatic tip. As would be recognized by one skilled in the art, other atraumatic tips could be used, such as those described in U.S. patent application Ser. No. 09/551,467, entitled "Catheter Having Mapping Assembly," the disclosure of which is incorporated herein by reference.

All of the electrode lead wires 50 and thermocouple wires 70 and 72 extend through the lead wire lumen 30 in the distal shaft 14. Within the proximal shaft 12, the wires extend through a protective tubing 36 to keep the wires from contacting other components extending through the central lumen 18. The protective tubing 36 is preferably anchored at its distal end to the proximal end of the distal shaft 14 by gluing it in the lead wire lumen 30 with polyurethane glue or the like. The electrode lead wires 50 then extend out through the control handle 16 and to a suitable monitoring device or source of ablation energy (not shown), as appropriate, via a suitable connector 60, as is generally known in the art. The thermocouple wires 70 and 72 similarly extend out through the control handle 16 and to a connector 62 connectable to a temperature monitor (not shown).

A puller wire 84 is provided for deflection of the distal shaft 14. The puller wire 84 extends through the proximal shaft 12, is anchored at its proximal end to the control handle 16, and is anchored at its distal end to the distal shaft 14. The puller wire 84 is made of any suitable metal, such as stainless steel or Nitinol, and is preferably coated with Teflon® or the like. The coating imparts lubricity to the puller wire 84.

A compression coil 86 is situated within the proximal shaft 12 in surrounding relation to the puller wire 84. The compression coil 86 extends from the proximal end of the proximal shaft 12 to the proximal end of the distal shaft 14. The compression coil 86 is made of any suitable metal, preferably stainless steel. The compression coil 86 is tightly wound on itself to provide flexibility, i.e., bending, but to resist compression. The inner diameter of the compression coil 86 is preferably slightly larger than the diameter of the puller wire 84. The Teflon® coating on the puller wire 84 allows it to slide freely within the compression coil 86. If desired, particularly if the lead wires 50 are not enclosed by a protective tubing 36, the outer surface of the compression coil 86 is covered by a flexible, non-conductive sheath 88, e.g., made of polyimide tubing, to prevent contact between the compression coil and any other wires within the proximal shaft 12.

The compression coil 86 is anchored at its proximal end to the outer wall 22 of the proximal shaft 12 by proximal glue joint 90 and at its distal end to the distal shaft 14 by distal glue joint 92. Both glue joints 90 and 92 preferably comprise polyurethane glue or the like. The glue may be applied by means of a syringe or the like through a hole made between the outer surface of the proximal shaft 12 and the central lumen 18. Such a hole may be formed, for example, by a needle or the like that punctures the outer wall 22 of the proximal shaft 12 that is heated sufficiently to form a permanent hole. The glue is then introduced through the hole to the outer surface of the compression coil 86 and wicks around the outer circumference to form a glue joint about the entire circumference of the compression coil 86.

Figure 5:
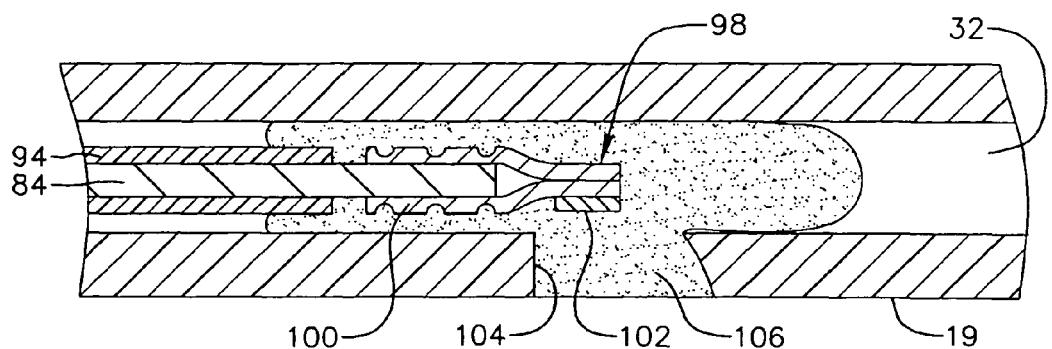
FIG. 5 is a cross sectional view of a portion of the catheter intermediate section showing one means for attaching the puller wire.
Figure 6:
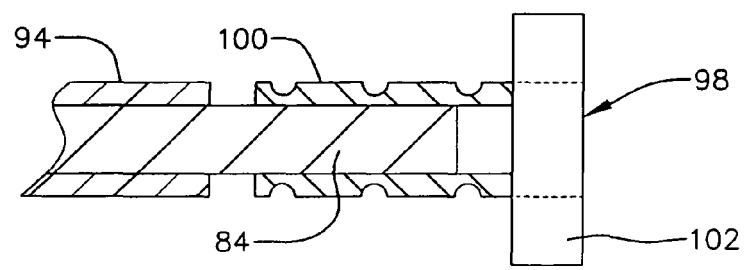
FIG. 6 is a top cross sectional views of a preferred puller wire anchor.
Figure 7:
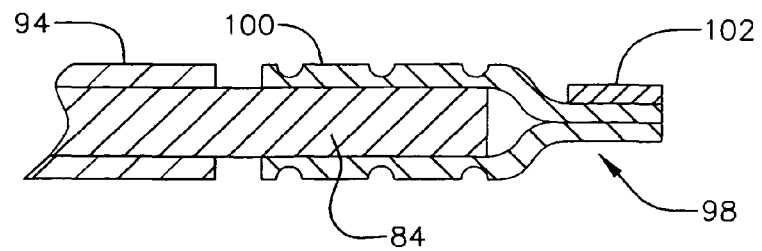
FIG. 7 is a side cross sectional views of the puller wire anchor of FIG. 6.

The puller wire 84 extends into the puller wire lumen 32 of the distal shaft 14. Preferably the puller wire 84 is anchored at its distal end to the side of the shaft 14, as shown in FIGS. 5 to 7. A T-shaped anchor 98 is formed which comprises a short piece of tubular stainless steel 100, e.g., hypodermic stock, which is fitted over the distal end of the puller wire 84 and crimped to fixedly secure it to the puller wire. The distal end of the tubular stainless steel 100 is fixedly attached, e.g., by welding, to a stainless steel cross-piece 102 such as stainless steel ribbon or the like. The cross-piece 102 sits in a notch 104 in a wall of the flexible tubing 19 that extends into the puller wire lumen 32 of the distal shaft 14. The stainless steel cross-piece 102 is larger than the opening and, therefore, cannot be pulled through the opening. The portion of the notch 104 not filled by the cross-piece 102 is filled with glue 106 or the like, preferably a polyurethane glue, which is harder than the material of the flexible tubing 19. Rough edges, if any, of the cross-piece 102 are polished to provide a smooth, continuous surface with the outer surface of the flexible tubing 19. Within the puller wire lumen 32 of the distal shaft 14, the puller wire 84 extends through a plastic, preferably Teflon®, puller wire sheath 94, which prevents the puller wire 84 from cutting into the wall of the distal shaft 14 when the distal shaft is deflected. Any other suitable technique for anchoring the puller wire 84 in the distal shaft 14 can also be used.

Longitudinal movement of the puller wire 84 relative to the proximal shaft 12, which results in deflection of the distal shaft 14, is accomplished by suitable manipulation of the control handle 16. Examples of suitable control handles for use in the present invention are disclosed, for example, in U.S. Pat. Nos. Re 34,502 and 5,897,529, the entire disclosures of which are incorporated herein by reference.

In use, a suitable guiding sheath is inserted into the patient. An example of a suitable guiding sheath for use in connection with the present invention is the Preface™ Braiding Guiding Sheath, commercially available from Biosense Webster (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the electrode assembly can be straightened to fit through the sheath, and it will return to its original shape upon removal of the sheath.

The proximal and/or distal mapping electrodes are then used to measure electrical activity in the region to be ablated. The porous electrode is used to ablate one or more continuous linear lesions by supplying the ribbon electrode with radio frequency energy or other ablation energy and simultaneously introducing fluid through the irrigation openings, into the open space and through the porous sleeve. As used herein, the terminology "linear lesion" refers to any lesion, whether curved or straight, between two anatomical structures in the heart that is sufficient to block a wavelet, i.e., forms a boundary for the wavelet. Anatomical structures, referred to as "atrial trigger spots", are those regions in the heart having limited or no electrical conductivity and are described in Haissaguerre et al., "Spontaneous Initiation of Atrial Fibrillation by Ectopic Beats Originating in the Pulmonary Veins", New England Journal of Medicine, 339: 659-666 (Sep. 3, 1998), the disclosure of which is incorporated herein by reference. The linear lesions typically have a length of from about 1 cm to about 6 cm, but can be longer or shorter as necessary for a particular procedure. The thermocouples or other temperature sensing means can be used to monitor the temperature of the tissue during ablation. The mapping, ablation and temperature measuring steps can be performed in any desired order. In one particular embodiment, the porous electrode is used to isolate the pulmonary vein by creating one or more lesions around the pulmonary vein.

In an alternative embodiment, the electrode assembly further includes a location sensor (not shown) for providing location information about the electrode assembly. Such a design is disclosed in U.S. patent application Ser. No. 10/199,525, entitled "Atrial Ablation Catheter and Method for Treating Atrial Fibrillation," the disclosure of which is incorporated herein by reference. Preferably the location sensor comprises a magnetic-field-responsive coil, as described in U.S. Pat. No. 5,391,199, or a plurality of such coils, as described in International Publication WO 96/05758. The plurality of coils enables six-dimensional position and orientation coordinates to be determined. Alternatively, any suitable position sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference.

If desired, two or more puller wires can be provided to enhance the ability to manipulate the intermediate section. In such an embodiment, a second puller wire and a surrounding second compression coil extend through the proximal shaft and into an additional off-axis lumen in the distal shaft. The first puller wire can be anchored proximal to the anchor location of the second puller wire. Suitable designs of catheters having two or more puller wires, including suitable control handles for such embodiments, are described, for example, in U.S. Pat. Nos. 6,123,699, 6,171,277, 6,183,435, 6,183,463, 6,198,974, 6,210,407, and 6,267,746, the disclosures of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for ablating heart tissue comprising:
   inserting into the heart of a patient the distal end of a catheter comprising:
      a non-conductive tubing mounted on the distal end of the catheter, a mid-section of the non-conductive tubing having a pre-formed generally heel-shaped curve comprising a first bend away from a central longitudinal axis of the catheter and a second bend back toward and past the central longitudinal axis of the catheter, wherein the non-conductive tubing terminates in a generally straight distal end that is generally transverse to the central longitudinal axis of the catheter; and
      a porous electrode arrangement comprising:
         a single, continuous coiled electrode wrapped around at least a portion of the non-conductive tubing, the single, continuous coiled electrode being electrically connectable to a suitable energy source;
         a porous sleeve mounted in surrounding relation to the coiled electrode and defining an open space between the porous sleeve and the coiled electrode; and
         one or more irrigation openings fluidly connecting the open space to a lumen extending through the catheter through which fluid can pass; and
   forming at least one linear lesion in the atrial tissue with the porous electrode arrangement by simultaneously supplying ablation energy to the single, continuous coiled electrode and introducing fluid through the lumen in the catheter, through the one or more irrigation openings, into the open space and through the porous sleeve.

2. The method of claim 1, wherein the generally straight distal end of the non-conductive tubing forms an angle with the longitudinal axis of the catheter ranging from about 75° to about 110°.

3. A method for ablating heart tissue comprising:
   inserting into the heart of a patient the distal end of a catheter comprising:
      a non-conductive tubing mounted on the distal end of the catheter, a mid-section of the non-conductive tubing having a pre-formed generally heel-shaped curve comprising a first bend away from a longitudinal centerline of the catheter and a second bend back toward and past the longitudinal centerline of the catheter, wherein the non-conductive tubing terminates in a generally straight distal end that is generally transverse to the longitudinal centerline of the catheter; and a porous electrode arrangement comprising:
- a single, continuous coiled electrode wrapped around at least a portion of the non-conductive tubing, the single, continuous coiled electrode being electrically connectable to a suitable energy source;
- a porous sleeve mounted in surrounding relation to the coiled electrode and defining an open space between the porous sleeve and the coiled electrode; and
- one or more irrigation openings fluidly connecting the open space to a lumen extending through the catheter through which fluid can pass; and forming at least one linear lesion in the atrial tissue with the porous electrode arrangement by simultaneously supplying ablation energy to the single, continuous coiled electrode and introducing fluid through the lumen in the catheter, through the one or more irrigation openings, into the open space and through the porous sleeve.

4. The method of claim 3, wherein the generally straight distal end of the non-conductive tubing forms an angle with the longitudinal centerline of the catheter ranging from about 75° to about 110°.

* * * * *